United States Patent [19]

Riley

[11] Patent Number: 4,997,056

[45] Date of Patent: Mar. 5, 1991

[54] EAR-FOCUSED ACOUSTIC REFLECTOR

[76] Inventor: Michael D. Riley, 1808 Pier St., Santa Monica, Calif. 90405

[21] Appl. No.: 304,495

[22] Filed: Jan. 31, 1989

[51] Int. Cl.⁵ .......................................... H05R 25/00
[52] U.S. Cl. .................................... 181/136; 181/129
[58] Field of Search ....................... 181/133, 136, 129

[56] References Cited

U.S. PATENT DOCUMENTS

| | | | |
|---|---|---|---|
| 1,621,629 | 3/1927 | Dawson | 351/158 X |
| 1,708,257 | 4/1929 | Campbell | 181/136 |
| 1,820,107 | 8/1931 | Agee | 181/136 |
| 2,228,024 | 1/1941 | Abrahams | 181/175 |
| 2,537,201 | 1/1951 | Amfitheatrof | 181/136 |
| 2,732,907 | 1/1956 | Leon | 181/175 |
| 3,723,962 | 3/1973 | Hotchner | 181/175 X |
| 3,938,616 | 2/1976 | Brownfield | 181/136 |
| 3,943,925 | 3/1976 | Leight | 351/158 X |
| 4,574,912 | 3/1986 | Fuss et al. | 181/129 |
| 4,768,613 | 9/1988 | Brown | 181/136 |
| 4,771,859 | 9/1988 | Breland | 181/136 |

FOREIGN PATENT DOCUMENTS 344526 6/1920 Fed. Rep. of Germany.
364066 6/1930 United Kingdom ................ 181/136

OTHER PUBLICATIONS

Chaba, "Earphones in Audiometry", J. Acoust. Soc. Am., vol. 83, No. 4, Apr. 1988, pp. 1688, 1689.

Primary Examiner—Benjamin R. Fuller
Attorney, Agent, or Firm—Flehr, Hohbach, Test, Albritton & Herbert

[57] ABSTRACT

An acoustic device for mechanically reflecting sound waves into the ear in an undistorted and directionally selective manner has a pair of movable acoustic reflectors constructed, configured and mounted to preserve accurately phase, frequency and image information in the sound waves of interest to the front of the user, secured to a headband or helmet in positions that place the focal points of the reflectors beyond the base of the lenses within the user's ear.

10 Claims, 5 Drawing Sheets

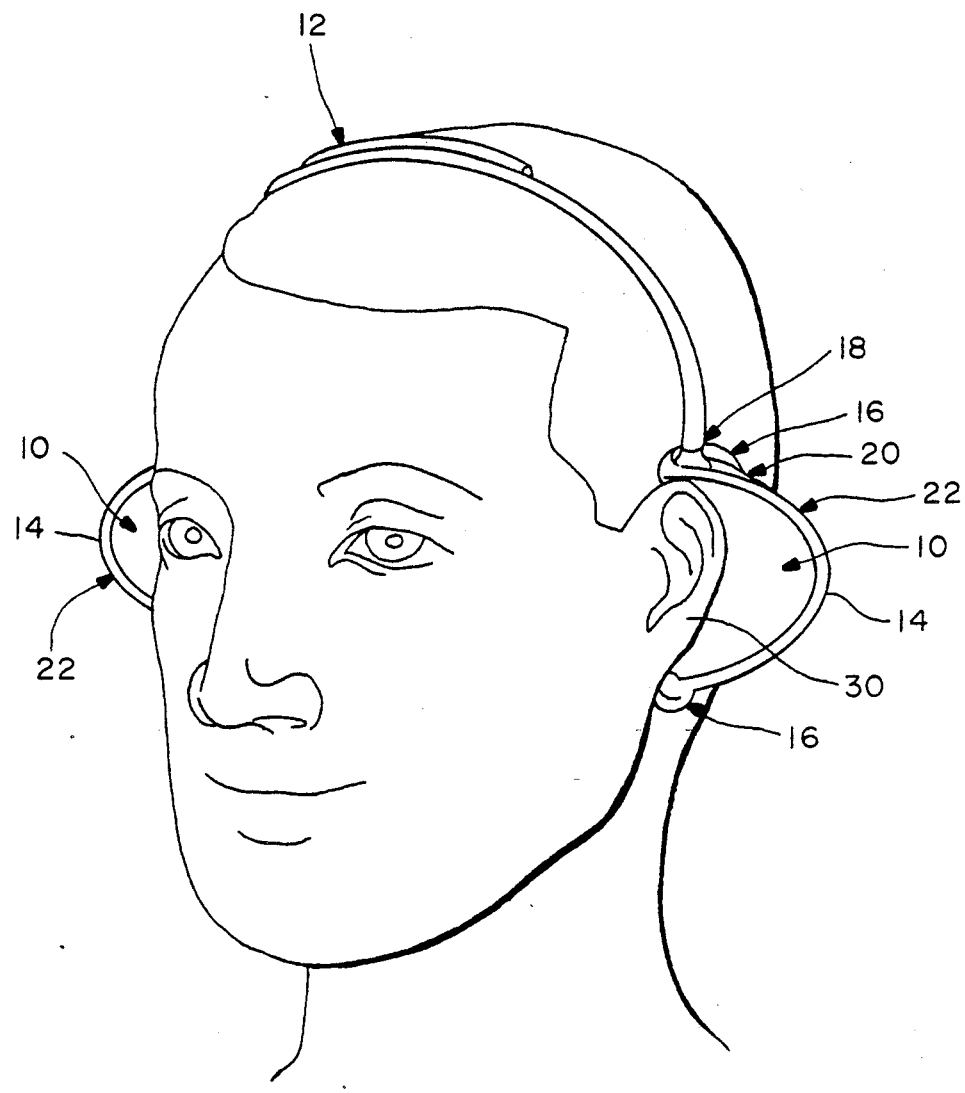
FIG.—1

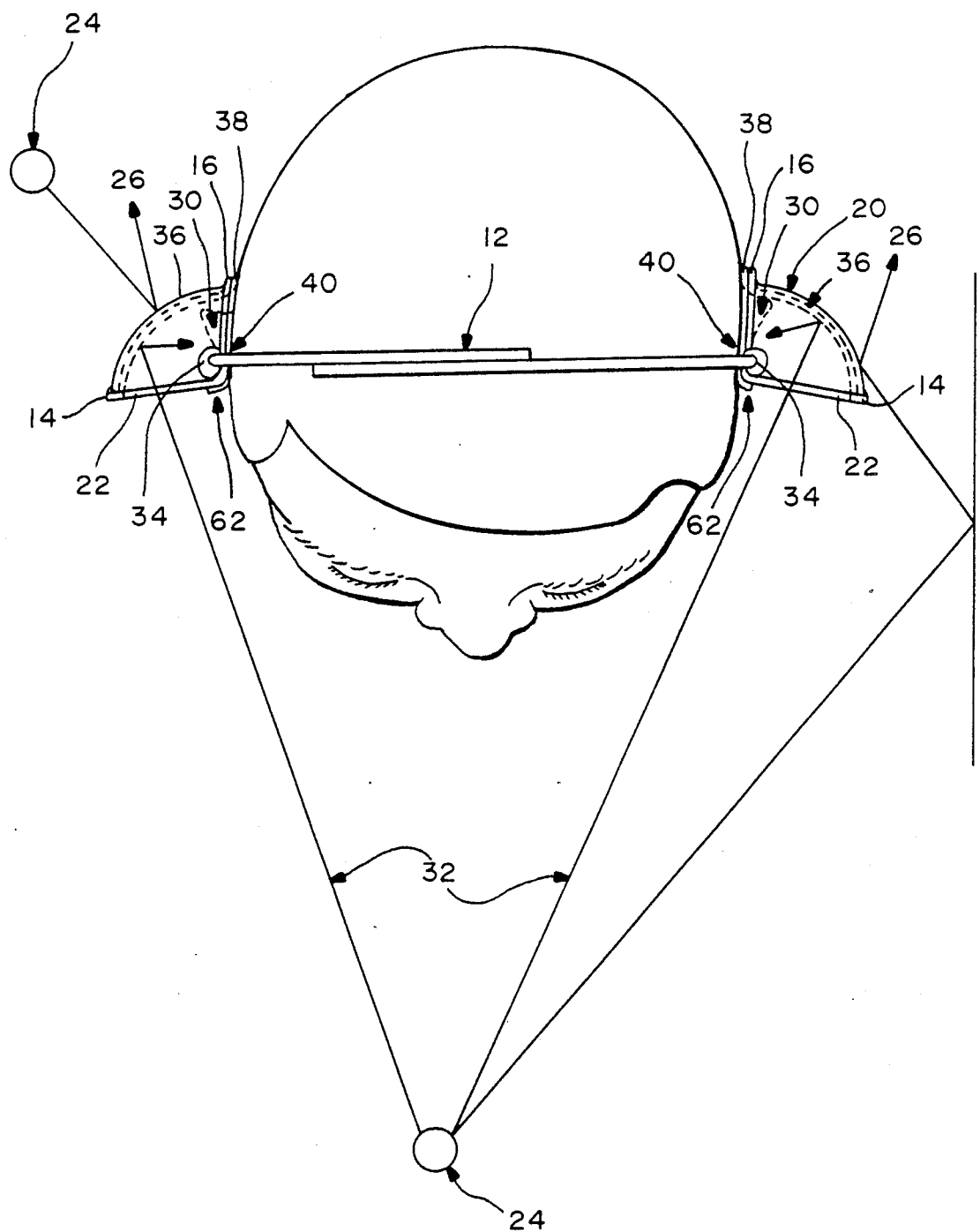
FIG.—2

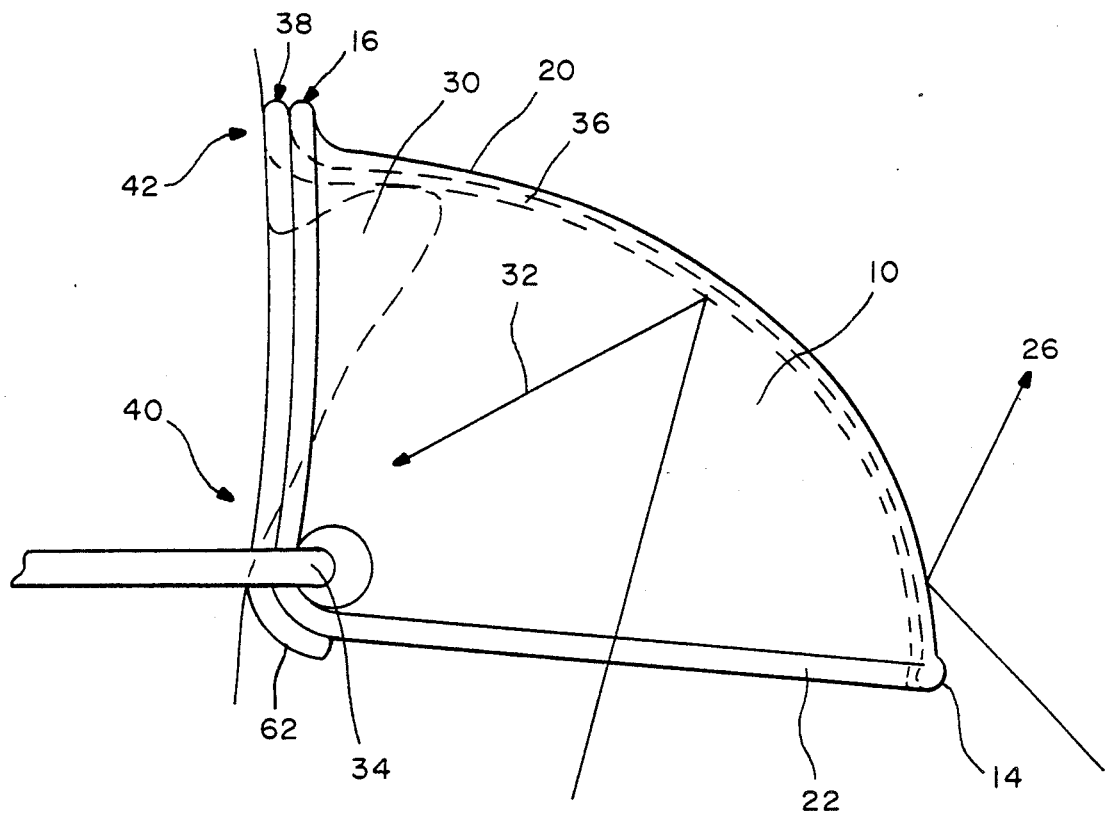
FIG.—3
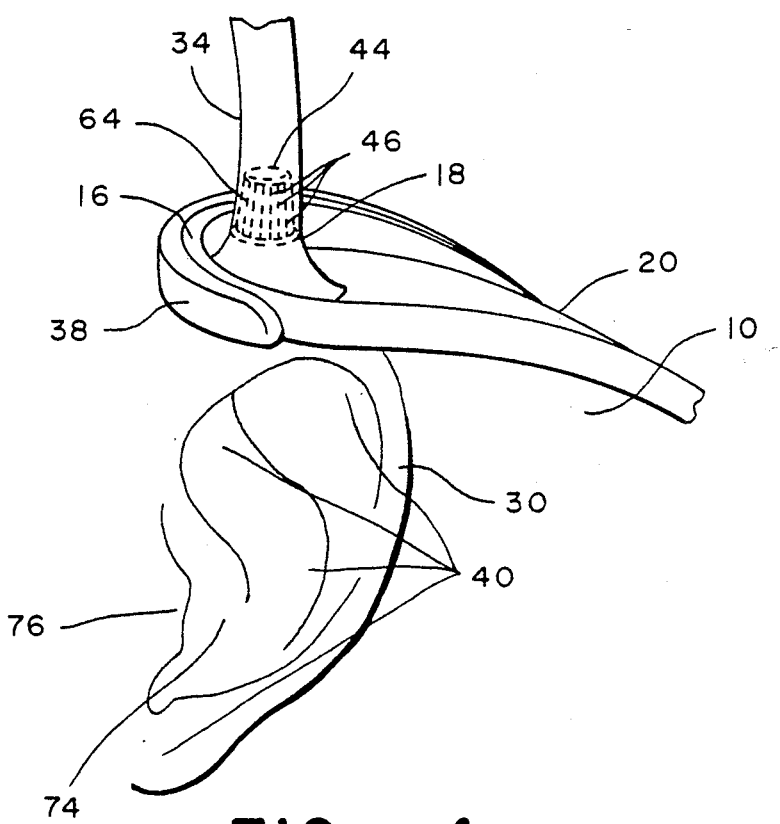
FIG.—4

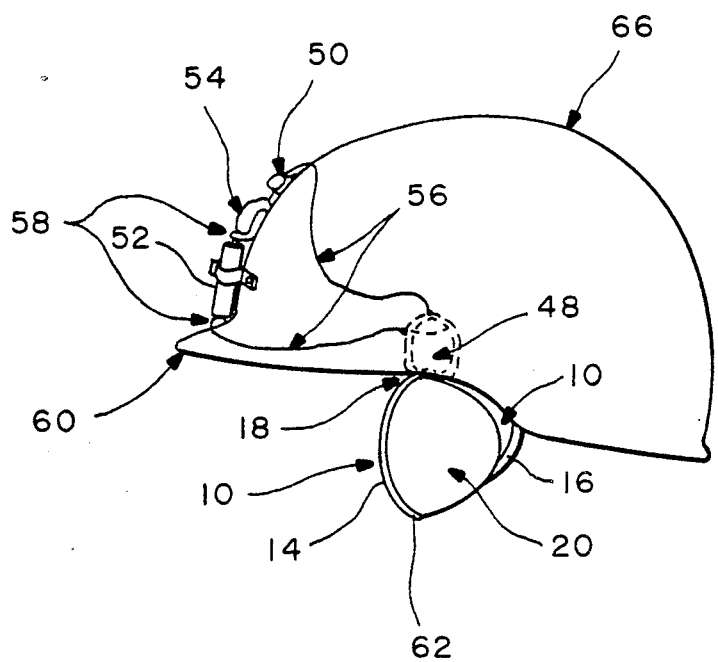
FIG.—5
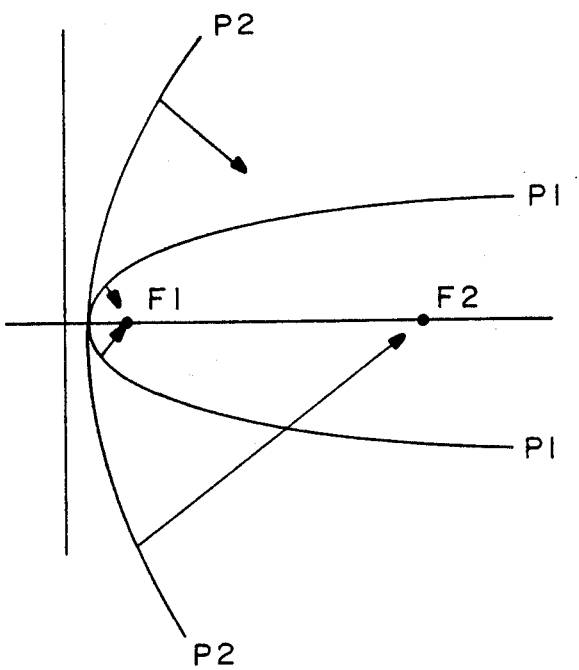
FIG.—6

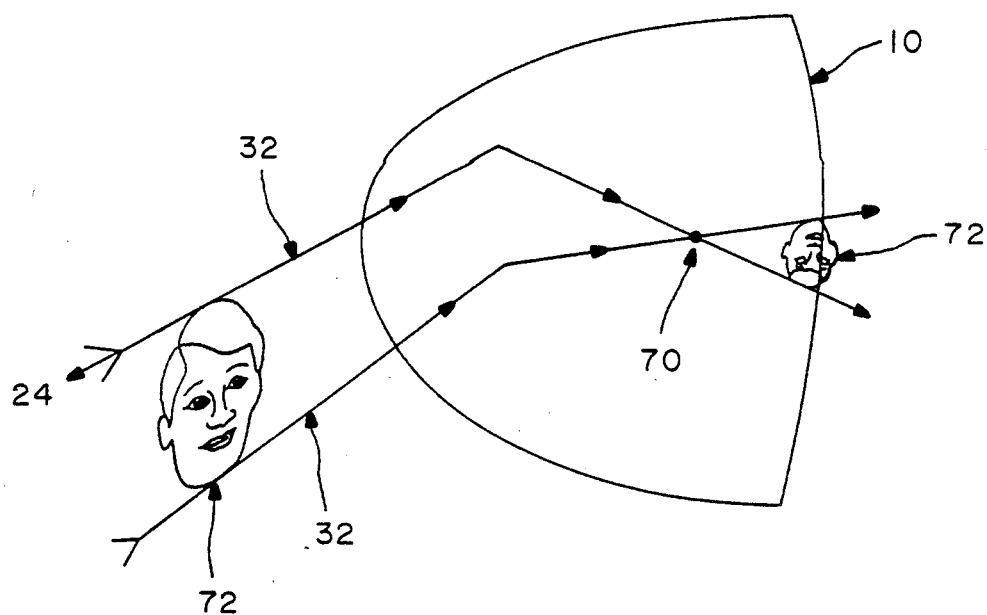
FIG.—7
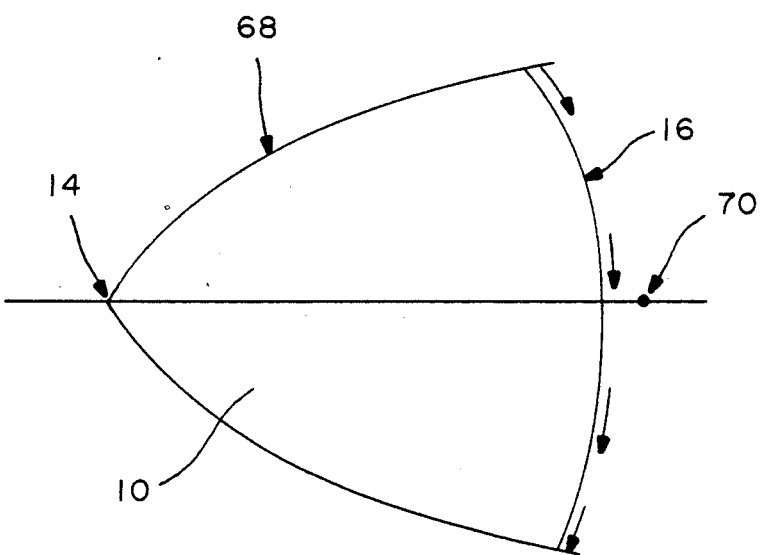
FIG.—8

EAR-FOCUSED ACOUSTIC REFLECTOR

BACKGROUND OF THE INVENTION

1. Field of the Invention

The present invention relates generally to novel improvements in devices for mechanically receiving larger amounts of sound waves than are received by normal human ears alone. More particularly, it relates to such devices for directing these waves into the ears of a user in a manner that preserves the greatest possible degree of information contained in those sounds that is of interest to the user. This invention also allows the user to selectively block out other noises that could either interfere with the perception of the information-bearing sound, or even damage the user's hearing due to excessive sound pressure levels. While prior art describes devices that can also mechanically increase the amount of sound received by the ear, none would perform this function with the degree of acoustic fidelity of the present invention.

Given a maximum frontal opening dimension of the present invention's acoustic reflector of roughly two inches, sound wave diffraction prevents this size reflector from providing substantial sound wave amplification benefits for under three kiloHertz. However, this size reflector help to improve perception of all sounds down to half this frequency by lowering the resonant frequency of the human ear canal from three kiloHertz to fifteen hundred kilohertz; this is accomplished by the reflector acting as an extension to the ear's canal duct which effectively doubles its length and thus halves its resonant frequency. Frequencies of these rates upward provide listeners with important speech notes and musical instruments' fundamental tones, and most of the harmonic overtones that convey information regarding speech and music's details, sound source locations, and the ambient space in which the sound originates.

2. Description of the Prior Art

Researchers in related electroacoustic fields have identified such phenomena as sound wave phase incoherence and frequency group delays as causes for reduced information delivery by sound waves. Group delay causes a loss of natural realism to the perception of sounds, especially transients; in terms of measurements, group delay is plotted as the slope, or first derivative function of, phase shift versus frequency, showing the amount of time delay that is undergone by signal components in different segments of the frequency spectrum perceptible to humans. "Folded exponential horn" systems, such as described in Deutsches Reich Patentschrift Nr. 344526, issued Nov. 23, 1921 and U.S. Pat. No. 3,938,616, issued Feb. 17, 1976 to Brownfield, can cause sound waves to acquire these kinds of distortions, by causing excessive reflections and resonances within the amplifying device itself.

Testing of active transducers (stereo headphones) used in close proximity to the ear has revealed that ". . . sound pressure produced at the eardrum is critically dependant on the wave properties of the earphone and the external ear. The geometry of the cavities coupling the earphone to the ear drum, which is affected by such factors as the positioning of the earphone on the head of the listener, becomes the most critical issue. These wave effects become important . . . at frequencies above about 2,000 Hertz . . . (sound pressures at the eardrum are) critically dependant on the geometry of the earphone and ear and the exact positioning of the earphone . . . "; from a letter by Zwislocki, Kruger, Miller, Niemoeller, Shaw and Studebaker appearing in the April, 1988 issue of the *Journal of the Acoustical Society of America*.

A variety of additional hearing assistance devices and related structures are known in the art, which do not deal with the perceptible effects of the geometry of the invented device in relationship to the ear of the user. For example, hearing assistance devices including a cup configured for positioning behind and extending outward beyond the user's ear are shown in the following issued U.S. Pat. Nos. 1,708,257, issued Apr. 9, 1929 to Campbell; 1,820,107, issued Aug. 25, 1931 to Agee; 2,537,201, issued Jan. 9, 1951 to Amfitheatrof; U.S. Pat. No. 4,574,912, issued Mar. 11, 1986 to Fuss et al. Somewhat related structures in combination With eyeglasses are disclosed in U.S. Pat. No. 1,621,629, issued Mar. 27, 1927 to Dawson and U.S. Pat. No. 3,943,925, issued Mar. 16, 1976 to Leight. None of these prior art devices overcome the problems with such devices discussed above.

A device mounted about the ear for the purpose of amplification of sounds that are frontally incident to the user can have the additional benefit of blocking direct and reflected sounds from the user's sides and rear. The so-called Haas Precedence Effect causes sounds side-reflected to the listener's ears within a twenty millisecond interval of their generation by a sound source to the listener's front (as from the walls of the room in which the user is listening to an audio system's loudspeakers, or to a "live" performer) will reduce the listener's ability to accurately identify the location of the frontal sound sources on the basis of auditory cues alone. Such reflected sounds represent noise for the listener who wishes to make such localizations accurately. Such wall-or-side-reflected sound which is blocked by a device mounted around a user's ear can still cause such a device to "ring" in response, if it is not properly "damped" by fabrication from or with a material or materials which will prevent such sympathetic vibrations. Such ringing would serve as a noise source which could diminish the user's ability to accurately locate frontally-incident sound sources. Also, any likewise-undamped mechanical sound conduction between the base of such a noise-ringing device and the skin-covered temporal and mastoid bones around and behind the user's ear could transmit the ringing and noise of reflected sound into the user's auditory system, by means of bone conduction of contact-induced vibration. No means to prevent these unwanted transmissions is specified in the prior art. While Brownfield's U.S. Pat. No. 3,938,616 and Fuss et. al.'s U.S. Pat. No. 4,574,912, both mentioned above, do indicate means of cushioning such contact areas for greater user comfort, such pads are not designed to have the desirable effects of damping the device's ringing or of preventing induced temporal and mastoid bone sound conduction.

SUMMARY OF THE INVENTION

Accordingly, it is an object of this invention to provide an acoustic device that mechanically receives a greater amount of sound waves than can the human ear alone, and that mechanically transmits those received sound waves into the user's ear or ears in a manner that preserves the phase-coherency, frequency balance, and even proper, upright vertical sonic image relationships in these sound waves, in a manner that will permit the user to perceive a more natural and intelligible amplification of only those sounds to which the user wishes to direct attention.

Another object is to provide this coherent amplification in a manner that will not call for the use of cosmetically objectionable large sizes for these acoustic devices.

Another object is to provide this amplification with a higher degree of directional selectivity, so that simply by moving the user's head to face the sound source of interest the user can choose the information to be amplified.

An additional object is to permit the user to quickly and easily reposition the acoustic reflector or reflectors that provide this amplification for better selectivity of source sounds.

A further object is to permit these acoustic reflectors to be quickly and conveniently repositioned by user into a fixed position that will actually reduce the amount of sound that arrives at the user's ears from an objectionably loud source to the user's front.

A still further object is to prevent the amplifying device itself from picking up spurious sound vibrations from sources not selected by the user and to prevent those sounds from entering the auditory system of the user.

A still further object is to permit the device to be used for a variety of functions, including two functions simultaneously—one for each ear.

Further objects of the invention will be identified as the description proceeds. The attainment of these and related objects may be achieved through use of the novel acoustic device that mechanically intercepts and reflects into an ear canal of a user a greater amount of frontally generated sound waves herein disclosed. The acoustic device does so in a manner that accurately preserves frontally-incident sound waves' phase coherency at all frequencies, and the virtual, non-inverted sonic images that these waves can represent. The device includes at least one acoustic reflector shaped to be worn circumferential to an external ear of the user. The at least one acoustic reflector has an apex positioned beyond the external ear and a head when worn. A focal point beyond the base of the at least one acoustic reflector is within the ear of the wearer. In particular, the at least one acoustic reflector preferably includes a layer of a non-reverberant material on a surface of the reflector, which may extend as well as a buffer between a base of the at least one acoustic reflector and the wearer's head.

The attainment of the foregoing and related objects, advantages and features of the invention should be more readily apparent to those skilled in the art, after review of the following more detailed description of the invention, taken together with the drawings, in which:

BRIEF DESCRIPTION OF THE DRAWINGS

FIG. 1 is a view of the invention in use on the listener's head, as seen facing the listener's front, from the user's left side.

FIG. 2 is a view of the invention in use on the listener's head, as seen looking down from above the listener's head from above, with the listener facing downward in the drawing.

FIG. 3 is an enlargement of the listener's left ear area as shown in FIG. 2, with a visualization of the path followed by one point in a typical sound wave with respect to its original source, its reflection from the acoustic reflector, and its arrival point at the surface of the ear.

FIG. 4 is an enlargement of the listener's left ear area as shown in FIG. 1, with a view of the racheted pivot and socket that holds the acoustic reflector and other modular devices in place against the listener's head.

FIG. 5 is a side view of a helmet equipped with sockets to hold the pivots of the acoustic reflector in place against the listener's head.

FIG. 6 is a depiction of the relationships between the focal points of "obtuse" and "acute" parabolas, their parabolic arcs and apices.

FIG. 7 is a view showing image-inverting effects of an ear-focused acoustic reflector with a focal point within volume of the reflector, rather than below the base of the reflector by means of visualization of the paths of top and bottom points of a sound wave which strikes the reflector and are reflected inward to the ear.

FIG. 8 is a depiction of the 180° axial rotation of a section of a parabola in order to generate a three dimensional shape with a relatively acute angle at its apex, where the axis of rotation intersects the edge of the shape so generated, and a single focal point on the axis of rotation at a point below the plane defined by all points at the ends of the parabolic sections opposite the apex, which plane forms a base to the generated shape.

DETAILED DESCRIPTION OF THE INVENTION

Turning now to the drawings on a descriptive basis, with similar reference characters denoting similar elements in all of the several views, FIGS. 1 through 4 illustrate an acoustic reflectors selective amplification of sound sources at which its frontal opening is pointed, mounted in a paired configuration on an adjustable headband 12.

Each acoustic reflector 10 is shaped in the form of a parabolic arc segment 68 rotated through 180°, as shown FIG. 8, in such a manner that the focal point 70 of the parabola of which the arc 68 is a segment lies below the base 16 of the acoustic reflector 10, and mounted to the headband 12 in such a manner that the open half of the reflector 10 faces to the front of the user. This shape forms a reflector 10 that reflects sound waves 32 from a frontal sound source 24 onto bowl 74 of the concha, that central portion of the external ear 40 that best serves to reflect sound from the inner backside of the tragus 76 into the opening of the ear canal. The base 16 of the acoustic reflector 10 surrounds the outer rear of the ear 30 when positioned in its fully set back position, for amplification of sound sources 24 to the user's front. The headband 12 is adjustable in both length and in pivot 18 angle, to permit maximum accommodation of the device to the size and shape of the user's head, for greater comfort and effectiveness.

The selection of a parabolic arc segment 68 as the basis for the shape of the acoustic reflector 10 is predicated on the unique ability of such a curve 68 to reflect waves of sound coherently to a single universal focal point 70 below the base 16 of the reflector, using a relatively compact reflector 10. If a pure paraboloid reflector shape had been used to deliver sound to a focal point 70 below the base 16 of the reflector 10, then as is shown in FIG. 6 the parabolic section of such a pure paraboloid, whether its grosser form was "acute" or "obtuse" in appearance, would have necessarily been a broad, flat dish shape that would be cosmetically unacceptable to prospective users. If the focal point 70 had been left within the volume of the reflector 10, then as shown in FIG. 7 the acoustic image 72 of the sound source to the user's front that is projected by the reflector 10 onto the ear 40 would be perceived as inverted, rather than as normally erect. FIG. 8 discloses the manner in which a segment of a parabolic arc 68 with an ideally positioned, sub-base 16 focal point 70 can be used to generate an optimally unobtrusive reflector shape 10 by means of a 180° rotation of the curve 68 about the axis formed by its focal point through the apex of curvature 14. The 180° rotation angle maximizes the parabolic area of the reflector 10 within a space of limited volume and thus maximizes: first, the degree of coherent reflection of the reflector to all of its interior surface; second, its rate of forward sound sources' 24 sound acceptance to a potential 180° hemisphere; and third, the desirable rejection of spurious noises 26 to the sides and rear of the user, all while minimizing the visual obtrusiveness of the device to non-users.

The outside surface 20 of the reflector is formed of a light but rigid material that retains an accurate lens shape, while the interior 36 and base 16 are lined with a material 38 such as rubber or silicone rubber that serves as an acoustic insulator and damper of acoustic ringing in the material of the reflector. This insulating material absorbs and dissipates heat the vibrations excited in the rigid material of the reflector by sounds 26 reflecting off of the back of the reflector. The continuous use of this damping material to cover the base 16 of the reflector 10 serves to prevent the rigid material of the reflector 10 from contacting the skin covering the mastoid bone 42 of the user, thus economically preventing bone conduction of sounds 26 picked up by the back of the reflectors. The damping of ringing of the material of the reflector 10 may also be effected by application of the damping material to the exterior back of the reflector, or to both the interior surface and exterior surface 20 of the reflector 10. The outer edge of the frontal opening of the reflector 10 is rounded at 22 in a manner that will reduce high frequency sound waves' diffraction, which can be produced by sharp or square edges.

The acoustic reflectors 10 are radially movable around a pivot 18, to permit the user to adjust their angle of frontal exposure and to focus on a closer sound source 24, thus increasing the reflectors 10 degree of rejection of reflected sounds 26 noise from sound sources 24 to the user's sides and rear. The reflectors 10 can be rotated to a fully forward position with their rounded edge 22 against 35 the user's cheeks, in which position sound sources 24 in front of and to the sides of the wearer will be blocked, reducing the user's perception of their sound volumes. Such a dual usage capability would be useful in noisy environments such as factories, where the user may wish to temporarily reduce the sound volumes received at the ears from machinery close to his front, yet at another time be able to hear someone speak from a distance despite high ambient noise levels. To make use of these alternative positions comfortably adjustable while the device is being worn, the corners 62 of the junctions between the forward edges 22 and the base are rounded.

The structure of the pivot 18 mechanism is modular, to permit the use of only one acoustic reflector 10 at a time if desired, or to permit the insertion of alternative functional modules into the receptacles 34 at the terminations of the headband 12. The pivot 18 mechanism employs a male post 44 at the top of the corners of the acoustic reflectors 10 which snap into and out of female receptacles 34. The male posts 44 and receptacle walls 34 are scored 46 with matching parallel grooves that permit the positions of the reflectors 10 to be fixed securely in any of a number of angular degrees of opening that might be useful to the user. To permit the angle at which the base 16 joins the headband 12 be determined automatically for the greatest comfort of the user, the receptacles 34 are formed with a flared, conical shape 64, so that the pivot post 44 may swivel with a limited degree of freedom.

FIG. 5 illustrates the acoustic reflectors 10 mounted on each side of a helmet 66, by means of a pivot 18 mounted to the sides of the helmet 46 shown with its bill 60 facing left. This version has an electric motor 48 at the pivot 18, to permit the user to move the reflectors 10 from behind the ears to a fully forward, sound blocking position, and back again, by means of a move of a single switch 50. This switch 50 activates the motors 48 by delivering power from a battery 52 mounted on, in or near the helmet 46. Wires 56 conduct current from the battery 52 through the contact points 58 to switch connecting wires 54 through the switch 50 in its open position, to the electric motor 48, in order to change the position of the acoustic reflectors 10. It should also be apparent that such moves or both reflectors 10 might be effected by one move implemented by such mechanical means as pulleys with cords, or levers.

The nature of the improvements embodied in this invention mechanically simplify and improve the performance of prior art, in the interests of economy of cost, greater fidelity, and broader utility. It is understood that its novel features, as shown and as described in the annexed claims, can be changed in its details of operation and configuration by those skilled in the art without departing from the essence of the invention.

It should further be apparent to those skilled in the art that various changes in form and details of the invention as shown and described may be made. It is intended that such changes be included within the spirit and scope of the claims appended hereto.

What is claimed is:

1. An acoustic device that mechanically intercepts and reflects into an ear canal of a user a greater amount of frontally generated sound waves in a manner that accurately preserves frontally-incident sound waves phase coherency at all frequencies, and virtual, non-inverted sonic images that the frontally incident sound waves can represent, comprising at least one acoustic reflector shaped to be worn circumferential to an external ear of the user, said at least one acoustic reflector having an apex positioned beyond the external ear and a base at an intersection of the external ear and head of the user when worn and a focal point beyond the base of said at least one acoustic reflector and within the ear of the user, said at least one acoustic reflector being configured so that:
  (a) a shape of said at least one acoustic reflector corresponds to that obtained by rotating C through 180° degrees about an axis formed by the focal point and the apex parabolic arc segment;
  (b) any portion of said at least one acoustic reflector is axially symmetrical from the apex to the focal point;
  (c) said at least one acoustic reflector can be set by positioning of the device to lie at or below surfaces of a concha in an interior of the external ear of the user; and (d) leading edges of said at least one acoustic reflector form an opening directed forward from the user.

2. An acoustic device as described in claim 1, wherein said at least one acoustic reflector comprises a pair of acoustic reflectors, one for each ear of the user.

3. An acoustic device as described in claim 1, wherein sounds from an identified source of special interest to the user can be selectively amplified by means of movement of the head in order to bring the focus of said at least one acoustic reflector to bear on the source of interest, and by means of adjustability of an angle of acceptance of said at least one acoustic reflector at a pivot point.

4. An acoustic device as described in claim 3, wherein sounds to the front or sides of the user that are objectionable can be reduced in amplitude by means of rotation of the position of said at least one acoustic reflector at the pivot to a forward, fixed-in-place position.

5. An acoustic device as described in claim 1, wherein said at least one acoustic reflector is further constructed and configured to preserve accurately information in desired, frontally-incident sound waves by diminishing reverberation of said at least one acoustic reflector as a source of undesirable noise by means of a layer of a non-reverberant material on at least one surface of said at least one acoustic reflector.

6. An acoustic device as described in claim 1, wherein said direct transmission of sounds reverberant in said at least one acoustic reflector into bones of the head in proximate contact with the base of said at least one acoustic reflector is diminished by means of a layer of a non-reverberant material as a buffer between the base of said at least one acoustic reflector and skin of the user.

7. An acoustic device as described in claim 1, wherein said at least one acoustic reflector is readably mounted on a head band.

8. An acoustic device as described in claim 1, wherein said at least one acoustic reflector may freely conform to the shape of the head of the user, by means of an adjustable-size headband and a pivot having a degree of freedom in an angle at which the headband connects to said pivot.

9. An acoustic device as described in claim 1, wherein said at least one acoustic reflector is incorporated into a headgear.

10. An acoustic device as described in claim 1, comprising an electric drive means connected to said at least one acoustic reflector for adjustment of position of said at least one acoustic reflector.

* * * * *

UNITED STATES PATENT AND TRADEMARK OFFICE
CERTIFICATE OF CORRECTION

PATENT NO. : 4,997,056

DATED : March 5, 1991

INVENTOR(S) : Michael D. Riley

It is certified that error appears in the above-identified patent and that said Letters Patent is hereby corrected as shown below:

Col. 6,
Claim 1, beginning at line 58, should read as follows:

(a) a shape of said at least one acoustic reflector corresponds to that obtained by rotating a parabolic arc segment through $180°$ about an axis formed by the focal point and the apex; --.

Signed and Sealed this

First Day of December, 1992

*Attest:*

DOUGLAS B. COMER

*Attesting Officer*      *Acting Commissioner of Patents and Trademarks*